United States Patent [19]

Cohan

[11] 3,935,640
[45] Feb. 3, 1976

[54] DENTAL INSTRUMENT

[76] Inventor: Richard Philip Cohan, No. 7 Hawkins Way, Larkspur, Calif. 94939

[22] Filed: Apr. 5, 1973

[21] Appl. No.: 348,386

[52] U.S. Cl.............................................. 32/40 R
[51] Int. Cl.² ........................................ A61C 3/00
[58] Field of Search ............ 128/2 S, 303 R, 92 EC; 32/50, 49, 40 R

[56] References Cited
UNITED STATES PATENTS

| | | | |
|---|---|---|---|
| 532,721 | 1/1895 | Dennis | 32/51 |
| 2,624,942 | 1/1953 | Wilborn | 32/41 |
| 3,480,003 | 11/1969 | Crites | 128/2 S |
| 3,727,314 | 4/1973 | DeAngeles | 32/41 |

FOREIGN PATENTS OR APPLICATIONS

| | | | |
|---|---|---|---|
| 9,796 | 2/1895 | France | 32/51 |

OTHER PUBLICATIONS

Ureteral Bougies, A.C.M.I., p. 37, American Cystoscope Makers, Inc., "Catheters and Accessories."

*Primary Examiner*—Robert Peshock
*Attorney, Agent, or Firm*—Townsend and Townsend

[57] ABSTRACT

A dental instrument comprising a metal shaft having a resilient extension at one end and a further functionally closely related instrument such as a periodontal probe or mirror at the other end. The resilient extension has two deformable surfaces which can be pressed against a tooth to test its mobility. The periodontal probe is color-coded, so that the depth to which the projection has been inserted into the gingival sulcus and any existing periodontal pocket is readily apparent to the dentist. The dental instrument can include a percussive hammer adjacent the resilient section.

10 Claims, 5 Drawing Figures

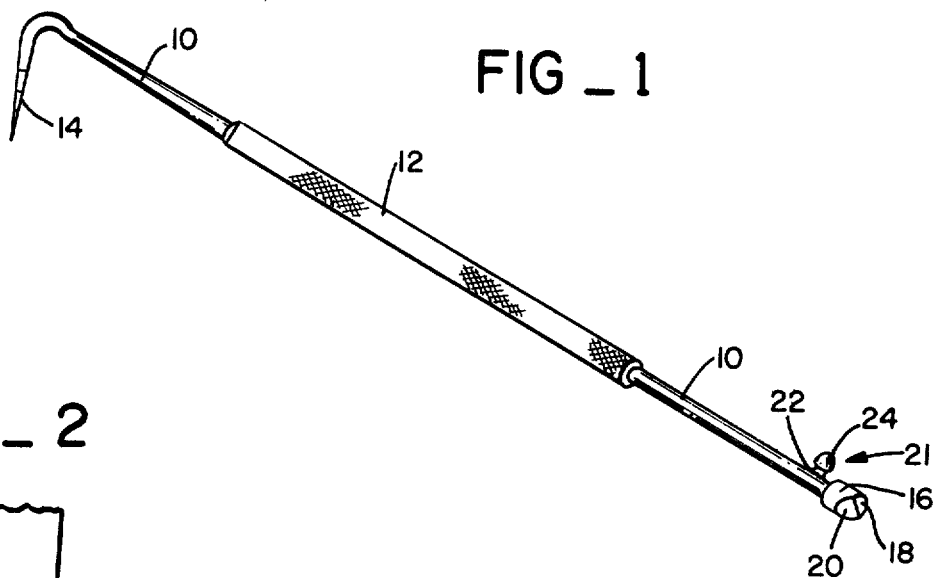
FIG_1
FIG_2
FIG_3
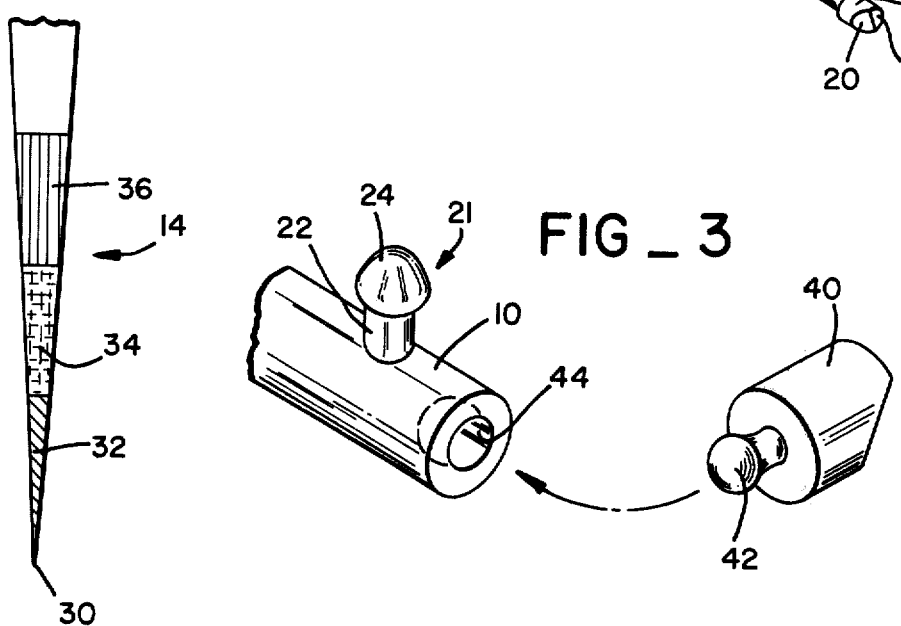
FIG_4
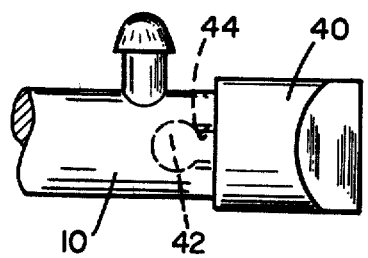
FIG_5
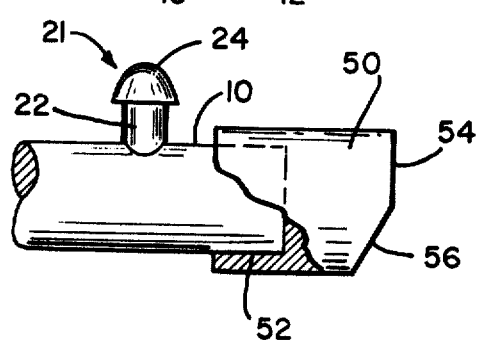

DENTAL INSTRUMENT

BACKGROUND OF THE INVENTION

This invention relates to dental instruments, and in particular to dental instruments for testing the various properties of a tooth and the investing periodontium.

When a dentist leaves dental school and enters actual practice, he often finds that various simple and mundane tests can be performed to determine the vitality of a tooth and health of the periodontium, and that such tests are often more practical and expeditious than the corresponding methods that he was taught in dental school. Unfortunately, commercially available dental instruments are usually designed according to the dictates of the dental school, rather than the practical needs of the dentist. Hence, he often lacks specific instruments designed to perform the practical tests which he himself has devised.

One of the tests often used by dentists in practice is simply pushing on the tooth to see whether it moves or not, thus testing the quality of the roots and investing osseous structures. Most dentists perform this mobility task with their fingers, or with the butt of an instrument normally having an entirely unrelated function. Another test used by dentists in their practice is to tap the tooth lightly with a metallic instrument, looking for a hyperresponse from the patient, to determine whether the interior of the tooth is inflamed and requires excavation or whether the external periapical area is inflamed or abscessed making it necessary to perform endodontic treatment. For this test, the dentist simply uses the side of one of his dental instruments.

Another problem which the dentist often encounters in practice is that dental instruments are designed for precision rather than convenience. This is particularly true of periodontal probes, which have accurate indicia which the dentist must read to determine the depth to which the probe has been inserted. However, the dentist only requires knowledge of the approximate depth of the probe rather than the exact depth to the fraction of a millimeter. Hence, reading such indicia is inconvenient and to a large extent unnecessary.

SUMMARY OF THE INVENTION

The present invention relates to dental instruments for performing the simple, yet practical, tests that a dentist wishes to perform in his day-to-day practice. Rather than rely on misuse of instruments designed for other purposes, or using his hands, the present invention provides instruments specifically related to performance of the desired tests.

The present invention provides a dental instrument comprising a metal shaft having a resilient deformable surface which can be used as a mobility probe. A percussive hammer, comprising a transverse projection on the metal shaft, can be located adjacent the resilient section. Also, a periodontal probe having a color-coded depth gauge, or a mirror or explorer, can be provided at the other end of the metal shaft.

The present invention provides dental instruments which meet the everyday needs of the dentist, and which do not involve misuse of existing instruments to perform desired tests. The instruments of this invention can be used by the dentist without difficulty, but still provide the dentist with the information he desires.

The novel features which are believed to be characteristic of the invention, both as to organization and method of operation, together with further objects and advantages thereof will be better understood from the following description considered in connection with the accompanying drawings in which preferred embodiments of the invention are illustrated by way of example. It is to be expressly understood, however, that the drawings are for the purpose of illustration and description only and are not intended as a definition of the limits of the invention.

BRIEF DESCRIPTION OF THE DRAWINGS

FIG. 1 is a perspective view of a dental instrument having a mobility probe and percussive hammer at one end and a periodontal probe at the other end.

FIG. 2 is a fragmentary view of the periodontal probe of FIG. 1.

FIG. 3 is a fragmentary view of an embodiment of the invention wherein the mobility probe has a protrusion insertable in a slot in the metal shaft of the dental instrument.

FIG. 4 illustrates the embodiment of FIG. 3 in the locked position.

FIG. 5 is a fragmentary view of an embodiment of the present invention wherein the mobility probe has a sleeve section which fits over the ends of the metal shaft of the dental instrument.

DESCRIPTION OF THE PREFERRED EMBODIMENT

A dental instrument incorporating the mobility probe, the percussive hammer and the color-coded periodontal probe of the present invention is illustrated by way of reference to FIG. 1. However, it is apparent that these elements need not be combined into a single tool, but that these features could be individually used on different dental instruments including mirrors and explorers.

Referring to FIG. 1, a metal shaft 10 having a central serrated portion 12 providing a convenient handle is illustrated. The metal shaft 10 has a pointed projection 14 at one end providing a periodontal probe. A resilient extension 16, formed of hard rubber or other suitable material, is secured at the other end of the metal shaft 10. Extension 16 has two deformable surfaces 18 and 20, one surface 18 substantially perpendicular to the longitudinal axis of the metal shaft 10 and the other surface 20 inclined approximately 45° thereto. The surfaces 18 and 20 are preferably serrated to give additional purchase on a tooth. Percussive hammer 21 comprising stem portion 22 and flanged striking portion 24 is located adjacent mobility probe 16. It will be appreciated by one skilled in this art that portion 12 could be provided with means for receiving various dental tools interchangeably at one or both ends thereof, such as disclosed in U.S. Pat. No. 797,270.

Periodontal probe 14 is illustrated in detail in the fragmentary view of FIG. 2. In the embodiment illustrated, periodontal probe 14 has transverse color-coded sections emanating from tip 30. Green section 32, yellow section 34 and red section 36 generally represent three millimeter increments from the tip 30. One skilled in this art will appreciate that the number of colored sections can be more or less. When periodontal probe 14 is inserted into periodontal tissue, the depth to which the probe has been inserted will be readily apparent to the dentist from the color-coded gauge and will not require the dentist to read detailed indicia on the periodontal probe. The series of colors green, yellow, and red are preferred since they represent a traditional warning scheme, but it is apparent that other color series, representing different increments from the tip, could be used as well.

Referring next to FIG. 3, an embodiment of the mobility probe is illustrated. Resilient extension 40 has protrusion 42 adapted to be inserted in corresponding slot 44 of metal shaft 10. Protrusion 42 has an enlarged end section which fits inside an enlarged portion of the slot 44 to lock resilient extension 40 to metal shaft 10 as illustrated in FIG. 4.

A second embodiment of the mobility probe is illustrated by way of FIG. 5. In this embodiment, resilient extension 50 has sleeve portion 52 extending from surfaces 54 and 56. This sleeve 52 fits over the end of metal shaft 10 to attach resilient extension 50 to metal shaft 10.

The dental instrument described above can be used to perform a variety of dental tests. For example, periodontal probe 14 can be used to determine the nature of the gingival crevice, e.g. Does it bleed? Is pus formation found? Are the tissues firm? Boggy? etc. In addition, periodontal probe 14 can be used to measure the depth of the gingival sulcus, the depth of the periodontal pocket, the amount of gingival recession on a tooth surface, and the width of the zone of attached gingiva. Surfaces 18 and 20 of mobility probe 16 can be pressed against a tooth to determine the mobility thereof. Two mutually inclined surfaces are provided so that the mobility of teeth in different locations can easily be tested. Striking surface 24 of percussive hammer 21 can impact upon a tooth to determine the vitality of the interior of the tooth and the investing periodontium. Hence, the dental instrument illustrated herein can be readily used to perform a variety of tests by which the dentist can determine the required treatment.

While preferred embodiments of the present invention have been illustrated in detail above, it is apparent that modifications and adaptations of the embodiments disclosed will occur to those skilled in the art. For example, it is not essential that the mobility probe, percussive hammer and periodontal probe form parts of a single device, rather, they could form parts of different devices. However, it is to be expressly understood that such modifications and adaptations are within the spirit and scope of the present invention, as set forth in the following claims.

What is claimed is:

1. A dental instrument comprising a metal shaft having an extension at one end thereof including a resilient, deformable surface thereon adapted to be pressed against a tooth to test the mobility of said tooth, and a periodontal probe at the other end of the metal shaft which includes a color-coded depth gauge.

2. A dental instrument comprising a metal shaft having an extension at one end thereof including a resilient, deformable surface thereon adapted to be pressed against a tooth to test the mobility of said tooth and wherein the resilient, deformable surface is serrated.

3. A dental instrument as recited in claim 1 wherein the extension includes a protrusion opposite the resilient, deformable surface, and wherein the metal shaft has a slot corresponding to the protrusion and adapted to receive said protrusion therein to fasten said extension to said shaft.

4. A dental instrument as recited in claim 1 wherein the extension includes a cylindrical sleeve portion adapted to extend from the surface of said extension in frictional engagement with the metal shaft.

5. A dental instrument as recited in claim 1 wherein the color-coded sections are progressively coded from the tip in shades of green, yellow and red to provide a traditional progressive warning indicator.

6. A dental instrument comprising a metal shaft having an extension at one end thereof including a resilient, deformable surface thereon adapted to be pressed against a tooth to test the mobility of said tooth and wherein the resilient, deformable surface has a pair of sections, the second section thereof inclined approximately 45° from the first section whereby mobility of teeth in different locations can be readily tested.

7. A dental instrument comprising a metal stem having a sharply pointed projection at one end forming a periodontal probe, said projection divided into transverse color-coded sections, whereby the depth to which the projection has been inserted in periodontal tissue is readily apparent, and wherein the color-coded sections are progessively coded from the tip in shades of green, yellow and red to provide a traditional progressive warning indicator.

8. A dental instrument as recited in claim 7 and additionally comprising an extension at the other end of the metal stem having a resilient, deformable surface to provide a mobility probe.

9. A dental instrument comprising a metal shaft having an extension at one end thereof including a resilient, deformable surface thereon adapted to be pressed against a tooth to test the mobility of said tooth, a transverse projection on the metal shaft adjacent to said extension and adapted to be used as a percussive hammer, and a periodontal probe at the other end of the metal shaft having a color-coded depth gauge so that the depth to which the projection has been inserted in periodontal tissue is readily apparent.

10. A dental instrument as recited in claim 9 wherein the resilient, deformable surface has a pair of sections, the second section thereof inclined approximately 45° from the first section so that mobility of teeth in different locations can be readily tested.

* * * * *